United States Patent
Bowers et al.

(10) Patent No.: US 12,239,745 B2
(45) Date of Patent: Mar. 4, 2025

(54) FORMULATION

(71) Applicant: OCUTEC LIMITED, Lanarkshire (GB)

(72) Inventors: Roderick Bowers, Lanarkshire (GB); Magdalena Switnicka-Plak, Lanarkshire (GB); Neil Graham, Lanarkshire (GB); James Carnegie, Lanarkshire (GB); Gordon Honeyman, Lanarkshire (GB); Abdul Rashid, Lanarkshire (GB)

(73) Assignee: Ocutec Limited, Lanarkshire (GB)

( * ) Notice: Subject to any disclaimer, the term of this patent is extended or adjusted under 35 U.S.C. 154(b) by 989 days.

(21) Appl. No.: 17/268,282

(22) PCT Filed: Aug. 13, 2019

(86) PCT No.: PCT/GB2019/052280
§ 371 (c)(1),
(2) Date: Feb. 12, 2021

(87) PCT Pub. No.: WO2020/035681
PCT Pub. Date: Feb. 20, 2020

(65) Prior Publication Data
US 2021/0316035 A1    Oct. 14, 2021

(30) Foreign Application Priority Data

Aug. 14, 2018 (GB) ...................... 1813229

(51) Int. Cl.
| | |
|---|---|
| A61L 12/12 | (2006.01) |
| A61L 15/22 | (2006.01) |
| A61L 15/42 | (2006.01) |
| A61L 29/08 | (2006.01) |
| A61L 29/14 | (2006.01) |
| G02B 1/04 | (2006.01) |

(52) U.S. Cl.
CPC .............. *A61L 12/12* (2013.01); *A61L 15/225* (2013.01); *A61L 15/42* (2013.01); *A61L 29/085* (2013.01); *A61L 29/14* (2013.01); *A61L 2420/06* (2013.01); *G02B 1/043* (2013.01)

(58) Field of Classification Search
CPC ........ A61L 12/12; A61L 15/225; A61L 15/42; A61L 29/085; A61L 29/14; A61L 2420/06; A61L 27/50; A61L 31/10; A61L 31/14; A61L 27/34; A61L 2/18; A61L 12/00; A61L 27/54; A61L 29/16; A61L 31/16; A61L 2202/24; G02B 1/043; A01N 33/02; A01N 31/02; A01N 37/02; A01N 57/12; A61K 31/765; A61K 31/78; A61K 31/785; A61P 31/04; C08K 5/092; C08L 71/02

See application file for complete search history.

(56) References Cited

U.S. PATENT DOCUMENTS

| | | |
|---|---|---|
| 6,699,435 B2 | 3/2004 | Salpekar et al. |
| 6,930,077 B2 | 8/2005 | Glick et al. |
| 7,037,469 B2 | 5/2006 | Hu et al. |
| 7,157,412 B2 | 1/2007 | Yu |
| 7,282,178 B2 | 10/2007 | Salamone et al. |
| 7,578,996 B2 | 8/2009 | Yu et al. |
| 8,119,112 B2 | 2/2012 | Xia et al. |
| 8,691,287 B2 | 4/2014 | Huth et al. |
| 8,759,321 B2 | 6/2014 | Burke et al. |
| 8,889,160 B2 | 11/2014 | Fridman |
| 9,926,515 B2 | 3/2018 | Jan et al. |
| 10,151,936 B2 | 12/2018 | Muya et al. |
| 10,584,307 B2 | 3/2020 | Ketelson et al. |
| 2003/0133905 A1 | 7/2003 | Hu et al. |
| 2003/0153475 A1 | 8/2003 | Hu et al. |
| 2004/0115270 A1 | 6/2004 | Jani et al. |
| 2005/0118132 A1 | 6/2005 | Xia et al. |
| 2005/0202986 A1 | 9/2005 | Hu et al. |
| 2006/0205621 A1 | 9/2006 | Borazjani et al. |
| 2006/0275173 A1 | 12/2006 | Borazjani et al. |
| 2006/0276359 A1 | 12/2006 | Borazjani et al. |
| 2006/0292105 A1 | 12/2006 | Lever et al. |
| 2007/0053948 A1 | 3/2007 | Ammon et al. |
| 2007/0142321 A1 | 6/2007 | Borazjani et al. |
| 2007/0148099 A1 | 6/2007 | Burke et al. |
| 2007/0203039 A1* | 8/2007 | Borazjani .............. C11D 1/008 510/112 |
| 2016/0136320 A1 | 5/2016 | Tucker et al. |
| 2017/0298296 A1 | 10/2017 | Jan et al. |
| 2018/0098937 A1 | 4/2018 | Horn |
| 2019/0225917 A1 | 7/2019 | Horn |

(Continued)

FOREIGN PATENT DOCUMENTS

| | | |
|---|---|---|
| CA | 2002534 | 5/1990 |
| EP | 1 706 473 B1 | 2/2008 |
| EP | 1 687 036 B1 | 8/2008 |
| EP | 1 976 571 B1 | 2/2009 |

(Continued)

OTHER PUBLICATIONS

International Search Report and Written Opinion in International Application No. PCT/GB2019/052280, mailed on Dec. 4, 2019.

*Primary Examiner* — Robert A Wax
*Assistant Examiner* — Quanglong N Truong
(74) *Attorney, Agent, or Firm* — Foley & Lardner LLP

(57) ABSTRACT

There is disclosed a formulation suitable for the reduction or prevention of contamination of articles by microorganisms. The formulation includes at least one block copolymer of ethylene oxide and propylene oxide, at least one polyacrylic acid salt, and at least one propoxylated ethylenediamine compound.

11 Claims, No Drawings

(56) References Cited

U.S. PATENT DOCUMENTS

2021/0181379 A1   6/2021  Zheng et al.
2021/0316035 A1  10/2021  Bowers et al.

FOREIGN PATENT DOCUMENTS

| JP | H04-193826 A | 7/1992 |
| JP | 2007-518714 A | 7/2007 |
| JP | 2015-197479 | 11/2015 |
| WO | WO-2007/073480 A1 | 6/2007 |
| WO | WO-2021/110975 A1 | 6/2021 |
| WO | WO-2021/156623 A1 | 8/2021 |

\* cited by examiner

FORMULATION

This application is the National Stage of International Patent Application No. PCT/GB2019/052280, filed Aug. 13, 2019, which claims the benefit of priority from European Patent Application No. 1813229.0, filed on Aug. 14, 2018, the content of each of which is incorporated by reference herein in its entirety.

The present invention relates to a formulation and its use in increasing the biocompatibility of a medical device with its intended biological environment and body fluids, examples include but are not limited to cardiovascular and urological catheters, cardiovascular and urological stents, central venous catheters, thoracic drain and urological drainage catheters, hydrocephalic shunts and wound dressings. Body fluids include blood, tears, lymph, cerebral spinal fluid, saliva, extra cellular fluid. In addition, the present invention relates to formulations which can minimise thrombogenic, the spoliation of contact lenses, blockage of catheters There is also provided the use of the formulation of the present invention in the prevention or reduction of contamination of medical devices by microorganisms, and in the prevention or reduction of the formation of biofilms on a surface of an article such as a medical device.

In addition, there is provided a method of increasing the wettability of the surface of an article such as a medical device through contact with the formulation of the present invention. There is also provided a method of reducing the contact angle of a surface of the surface of an article such as a medical device through contact with the formulation of the present invention. According to a further aspect, the present invention provides a surface by applying the formulation described herein to the surface.

The treatment of medical devices with the formulation of the present invention tends to increase their associated biocompatibility. Accordingly, treatment with the formulation of the present invention, increases the biological mechanical, physical and bulk properties of such medical devices contacting a surface of the human body, both initially and following extended periods of contact. By so doing the performance of the medical device is increased.

BACKGROUND TO THE INVENTION

Articles formed from polymeric materials which are used to manufacture medical devices often trigger the irreversible binding of protein lipids, eukaryotic and prokaryotic cells. This triggers the rejection of these devices by the body or deterioration of the performance of the device. The binding of proteins, lipids and cells can be related to polymers which show poor wetting characteristics with biological fluids such as blood, tears, lymph, cerebral spinal fluid, saliva and extra cellular fluid. Such problems are acute where the articles contact the surface of the eye, an internal surface of the body, or a mucous membrane.

The addition of silicone into polymers brings a number of benefits to the performance of the medical device, such as flexibility in catheters such as Foley catheters used to drain the bladder. Similarly, the inclusion of silicone into contact lenses has increased the oxygen permeability across the lens, thereby increasing corneal health by reducing the adverse effect of hypoxia. However, the incorporation of silicone is often associated with an increase in the hydrophobicity at the surface of the device. The addition of a silicone containing component in the manufacture of a polymers, such as polyurethane polymers, is associated with increased surface wettability problems. This in term can lead to a reduction of the surface wettability of the device which in turn triggers of the irreversible adsorption of proteins, lipids, immunoglobins, complement, macrophages as well as bacteria.

In the case of hydrogel contact lenses manufactured from methacrylate based polymers there is a well acknowledged problem of wearer discomfort and an increased risk of microbial infection caused by insufficient surface wettability for on-eye devices such as contact lenses and for indwelling medical devices such as joint prostheses, dental implants, catheters and cardiac implants.

In addition, insufficient surface wettability of such medical devices is associated with increased risk of biofilm formation. A microbial biofilm is a community of microbial cells embedded in an extracellular matrix of polymeric substances and adherent to a biological or a non-biotic surface. A range of microorganisms (bacteria, fungi, and/or protozoa, with associated bacteriophages and other viruses) can be found in these biofilms. Biofilms are ubiquitous in nature, are commonly found in a wide range of environments. Biofilms are being increasingly recognised by the scientific and medical community as being implicated in many infections, and especially their contribution to the recalcitrance of infection treatment.

Biofilms are etiologic agents for a number of disease states in mammals and are implicated in infections associated with medical devices designed to be used in or on the human body, in particular contact lens contamination, and infections of indwelling medical devices such as joint prostheses, dental implants, catheters and cardiac implants.

Saline is known for the storage of medical devices such as contact lenses. Other known storage formulations include disinfectants, buffering agents and surfactants.

WO2008/144494 discloses phospholipid compositions for contact lens care and preservation of pharmaceutical compositions.

Surprisingly, through appropriate selection of reagents the present invention provides an effective formulation for the treatment of medical devices, in particular to increase surface wettability and to increase associated biocompatibility. Comfort associated with contact of medical devices with the human body is increased accordingly, both initially and following extended periods of wear.

The formulation of the present invention improves the surface wettability of articles which it contacts, in particular articles formed from polyurethanes, and silicone-containing polymers, such as silicone-containing polyurethanes. Surprisingly, the formulation of the present invention also reduces the binding of lipids proteins to surfaces of the article, and reduces the risk of formation of biofilms on the medical devices.

The formulation of the present invention may also be for used in a method of reducing platelet aggregation on or at the treated surface(s) of the article and reducing the propensity of formation of thrombosis or blood clots on or at the treated surface(s) of the article.

STATEMENT OF INVENTION

According to a first aspect of the present invention, there is provided a formulation comprising:
  a. 0.1 to 7 wt. % of at least one block copolymer of ethylene oxide and propylene oxide, generally having the structure of ethylene oxide-propylene oxide-ethylene oxide;
  b. 0.1 to 5 wt. % of at least one polyacrylic acid salt;

c. 0.01 to 3 wt. % of at least one propoxylated ethylenediamine compound.

The higher the contact angle and the higher the frictional properties associated with the surface of a medical device designed for contact with a biological fluid, the less comfortable the medical device, both initially and following extended periods of contact.

Surprisingly, the formulation of the present invention decreases the contact angle of medical devices which are contacted therewith, increasing the surface wettability thereof and improving the comfort of the medical devices both initially and following extended periods of contact with biological fluid and/or wear. This is achieved through appropriate selection of components and their concentrations. The storage formulation is particularly effective for articles formed from polyurethane polymers, including those comprising silicone. Particular mention may be made of contact lenses and catheters in this regard.

Generally, a medical device is treated in a receptacle comprising the formulation of the present invention. Following such storage, the contact angle of surface(s) of the medical device is generally reduced for more than 30 minutes, generally more than one hour, typically more than 5 hours, generally more than 12 hours, suitably for around 24 hours after removal from the receptacle. Whilst the applicant does not wish to be bound by theory, this is likely due to the formulation of the present invention being absorbed onto the surface(s) of the medical device and/or into the medical device, the formulation may then be released from the medical device following removal of the medical device from the receptacle. The contact angle of the surface(s) of the medical device may return to their original value after extended periods following removal from the receptacle, but the contact angle can repeatably be reduced by replacing the medical device into the receptacle.

In addition, adding the formulation of the present invention to surface(s) of an article reduces associated protein absorption and reduces associated bacterial absorption to the surface(s) thereof, compared to an equivalent medical device which has not been treated through contact with the formulation of the present invention. This is useful in preventing or reducing the risk of formation of thrombosis on the surface, as well as preventing, or reducing the risk of formation of biofilms.

According to one embodiment, the formulation comprises:
a. 0.2 to 5 wt. % of at least one block copolymer of ethylene oxide and propylene oxide, generally having the structure of ethylene oxide-propylene oxide-ethylene oxide;
b. 0.3 to 2 wt. % polyacrylic acid alkali metal salt, generally a polyacrylic acid sodium salt;
c. 0.01 to 3 wt. % of at least one propoxylated ethylenediamine compound having the structure of Formula A:

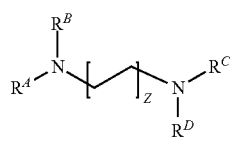

where at least one (generally all) of $R^A$ to $R^D$ have the structure of R below:

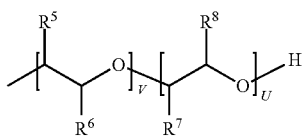

any of $R^A$ to $R^D$ not having the structure R represent a hydrocarbyl compound (generally a diamine hydrocarbyl compound) or H;

Z is an integer of from 1 to 10, generally 1 to 5, suitably 1 or 2, typically 1;

where $R^5$ to $R^8$ independently represent a small alkyl group or H, where at least one of $R^5$ to $R^8$ represents a small alkyl group, typically $C_1$ to $C_5$ alkyl group, generally methyl (typically 1 to 3 of $R^5$ to $R^8$ independently represent $C_1$ to $C_5$ alkyl group);

V and U are integers independently selected from 1 to 100, generally independently selected from 30 to 100, typically independently selected from 20 to 60, suitably independently selected from 50 to 100, where the sum of V and U is generally less than 150;

d. at least 90 wt. % solvent, generally water, suitably deionized water.

According to a further aspect of the present invention, the formulation disclosed herein comprises a compound including one or more phosphate groups, in particular a compound comprising a hydrophilic head group (for example a choline head group) and one or more hydrophobic phosphate containing tail group(s). According to one embodiment, the compound including one or more phosphate groups comprises a choline group (for instance glycerol phosphorylcholine (GPC)). The compound including one or more phosphate groups may be a phospholipid.

According to one embodiment, there is provided a method of reducing or preventing contamination of articles by microorganisms comprising contacting the article with the formulation as described herein.

There is also provided the use of the formulation described herein as a treatment formulation, in particular for a medical device such as an ophthalmic device or an in-dwelling medical device such as those disclosed herein, for instance a catheter.

Contact with the formulation as described herein generally reduces or prevents contamination of articles by microorganisms.

The formulation described herein is suitable for a medical device which contacts tissue and/or biological fluid in the course of its operation or utility, in particular contacts a biological fluid such as blood, tears, saliva and/or mucous in the course of its operation or utility, generally tears. According to a further aspect of the present invention there is provided a substrate comprising the formulation described herein.

Treatment of a device through contact with the formulation described herein increases the associated biocompatibility of the device.

According to one aspect, there is provided a method of increasing the surface wettability of a device comprising contacting a surface of the device with the formulation as described herein.

According to a further aspect of the present invention, there is provided a method of decreasing the contact angle of a surface of a device comprising contacting the surface with the formulation as described herein.

According to a further aspect of the present invention, there is provided a method of reducing or preventing binding of proteins and/or lipids to a surface of a device comprising contacting the surface with the formulation as described herein.

According to a further aspect of the present invention there is provided the formulation as described herein for use in the treatment or prevention of the formation of a microbial biofilm.

There is also provided a method of preventing biofilm formation on or in a medical device comprising administering the formulation as described herein to at least one surface of the medical device.

There is also provided a method of reducing platelet aggregation on or at a surface by applying the formulation described herein to the surface.

According to a further embodiment there is provided a kit of parts including a receptacle containing the formulation as described herein and instructions for use.

Throughout the Application, where a composition or formulation is described as having, including, or comprising specific components, or where processes are described as having, including, or comprising specific process steps, it is contemplated that the composition or formulation of the present teachings also consist essentially of, or consist of, the recited components, and that the processes of the present teachings also consist essentially of, or consist of the recited process steps.

In the Application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes", "including,", "comprise", "comprises" "comprising", "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

It should be understood that the order of steps or order for performing certain actions is immaterial so long as the present teachings remain operable. Moreover, two or more steps or actions may be conducted simultaneously.

Features, integers, characteristics, compounds, chemical moieties or groups described in conjunction with a particular aspect, embodiment or example of the invention are to be understood to be applicable to any other aspect, embodiment or example described herein unless incompatible therewith.

DETAILED DESCRIPTION

Definitions

"DK" is a measure of the oxygen permeability of a material provided in Barrer units where 1 Barrer=$10^{-11}$ $cm^2 \cdot mL \cdot mmHg$.

The term "small alkyl group" refers to an alkyl group having a carbon backbone of 1 to 6 carbon atoms, typically 1 to 4 carbon atoms.

The term "alkenyl" includes straight or branched chain hydrocarbon groups having 1 to 30 carbon atoms with at least one carbon-carbon double bond, the chain being optionally interrupted by one or more heteroatoms. The chain hydrogens may be substituted with other groups, such as, halo, —$CF_3$, —$NO_2$, —$NH2$, —CN, —$OCH_3$, —$C_6H_5$, —O—$C_6H_5$O-alkyl, —O—$C_6H_5$O-alkenyl, p-NHC(=O)—$C_6H_5$—NHC(=O)—$CH_3$, —CH=NH, —NHC(=O)-Ph and —SH. Preferred straight or branched alkenyl groups include allyl, ethenyl, propenyl, butenyl pentenyl, hexenyl, heptenyl, octenyl, nonenyl, decenyl, undecenyl, dodecenyl, tridecenyl, tetradecenyl, pentadecenyl or hexadecenyl.

The term "alkyl" includes straight or branched chain aliphatic hydrocarbon groups that are saturated and have 1 to 30 carbon atoms. The alkyl groups may be interrupted by one or more heteroatoms, such as oxygen, nitrogen, or sulfur, and may be substituted with other groups, such as, halo, —$CF_3$, —$NO_2$, —$NH_2$, —CN, —$OCH_3$, —$C_6H_5$, —O—$C_6H_5$O-alkyl, —O—$C_6H_5$O— alkenyl, p-NHC(=O)—$C_6H_5$—NHC(=O)—$CH_3$, —CH=NH, —NHC(=O)-Ph and —SH. Preferred straight or branched alkyl groups include methyl, ethyl, propyl, isopropyl, butyl, t-butyl, sec-butyl, pentyl, hexyl, heptyl, octyl, nonyl, decyl, undecyl and dodecyl, tridecyl, tetradecyl, pentadecyl or hexadecyl.

The term "halo" means an element of the halogen family. Preferred halo moieties include fluorine, chlorine, bromine or iodine.

"Biocompatible", as used herein, refers to a material or surface of a material, which may be in intimate contact with tissue, blood, or other bodily fluids of a patient for an extended period of time without significantly damaging the tissue or cell environment, in particular the ocular environment and without significant user discomfort.

Number average molecular weights described in the text are those determined experimentally within the applicant's laboratories by end group analysis and/or provided by the manufacturer.

The term "substituted" as used herein in reference to a moiety means that one or more, especially up to 5, more especially 1, 2 or 3, of the hydrogen atoms in said moiety are replaced independently of each other by the corresponding number of the described substituents. The term "optionally substituted" as used herein means substituted or unsubstituted.

It will, of course, be understood that substituents are only at positions where they are chemically possible, the person skilled in the art being able to decide (either experimentally or theoretically) without inappropriate effort whether a particular substitution is possible. For example, amino or hydroxy groups with free hydrogen may be unstable if bound to carbon atoms with unsaturated (e.g. olefinic) bonds. Additionally, it wall of course be understood that the substituents described herein may themselves be substituted by any substituent, subject to the aforementioned restriction to appropriate substitutions as recognised by the skilled man.

Where two or more moieties are described as being "each independently" selected from a list of atoms or groups, this means that the moieties may be the same or different. The identity of each moiety is therefore independent of the identities of the one or more other moieties.

Formulation

According to a first aspect of the present invention, there is provided a formulation comprising:
 a. 0.1 to 7 wt. % of at least one block copolymer of ethylene oxide and propylene oxide, generally having the structure ethylene oxide-propylene oxide-ethylene oxide;
 b. 0.1 to 5 wt. % of at least one polyacrylic acid salt;
 c. 0.01 to 3 wt. % of at least one propoxylated ethylenediamine compound.

The formulation of the present invention reduces the contact angle of a polymeric surface to which it is applied, in particular a polyurethane surface. This increases the wettability of the surface, and the associated comfort of the surface when contacting a surface of a human or animal body. In addition, the formulation of the present reduces the propensity of protein and/or lipids to adhere to the surface, as well as the propensity of micro-organisms such as bacteria to adhere to the surface reducing the risk of formation of a biofilm thereon. Binding of proteins, lipids and/or micro-organisms to a surface increases the hydrophobicity of the surface resulting in decreased biocompatibility. By reducing binding of proteins, lipids and/or micro-organisms onto a surface, the associated biocompatibility of the surface is increased, increasing the comfort of wear.

The contact angle of a polyurethane surface is generally reduced by at least 30°, typically by 35 to 45°, suitably by around 40° (suitably from around 60° to around 20°) following contact with 1 to 10 mL, generally 1 to 7 mL, suitably 5-7 mL, typically 1-2 mL of the formulation of the present invention per $cm^2$ surface.

The formulations of the invention may also find application as a treatment formulation. In this context, the formulations of the invention may be applied, either alone or in combination with other agents, to a surface to be treated. As used herein a "surface to be treated" may be a substrate as defined herein and may include medical devices, in particular ophthalmic devices and indwelling devices such as catheters.

Generally, there is provided an aqueous formulation. However, carriers or solvents other than water may find utility.

The formulation may be in the form of a gel, hydrogel, lotion, solution, cream, suspension, liquid or ointment. Generally, the formulation is an aqueous solution.

The formulation generally comprises more than 80 wt. % carrier liquid or solvent, typically more than 90 wt. % carrier liquid or solvent, generally more than 95 wt. % carrier liquid or solvent. Typically, the carrier liquid or solvent is water.

The formulation generally has a pH of 6.8 to 7.8.

Block Copolymer

The formulation of the present invention includes 0.1 to 7 wt. % of at least one block copolymer of ethylene oxide and propylene oxide, generally comprising terminal hydroxyl groups.

According to one embodiment, the copolymer of poly(ethylene glycol) (PEG) and polypropylene glycol (PPG) comprises alternating PEG and PPG groups; typically comprising, consisting or consisting essentially of the structure PEG-PPG-PEG or PPG-PEG-PPG.

Alternatively the copolymer may comprise, consist or consist essentially of the structure PEG-PEG-PPG or PPG-PPG-PEG.

Suitably the copolymer comprises 50 to 80 wt. % PPG, suitably around 70 wt. % PPG.

The copolymer may comprise 20 to 50% PEG, generally around 30% PEG.

According to one embodiment, the PEG and PPG blocks are present in a ratio of PEG:PPG in a ratio of 1:2 to 4.

The terminal hydroxyl groups of the copolymer may be primary or secondary hydroxyls, or a mixture thereof.

According to one embodiment, the terminal OH groups are secondary hydroxyls (e.g. derived from propylene oxide units).

Alternatively or additionally the terminal OH groups may be primary hydroxyls (e.g. derived from ethylene oxide units).

The formulation generally includes 0.1 to 5 wt. % of at least one block copolymer of ethylene oxide and propylene oxide, suitably 0.1 to 4 wt. %, typically 0.2 to 2 wt. %, more generally 0.2 to 1 wt. %, preferably 0.3 to 0.7 wt. %.

The formulation may include more than one copolymer or block copolymer.

The block copolymer is generally a diol.

The incorporation of the block copolymer (generally PEG-PPG-PEG or PPG-PEG-PPG) is believed to reduce or prevent micro-organism adhesion to a surface to which the formulation has been applied, in particular bacterial adhesion. In addition, the incorporation of the block copolymer may limit protein adhesion to a surface to which the formulation has been applied.

The number average molecular weight of the block copolymer is generally less than 20,000, suitably less than 15,000, typically less than 10,000. According to one embodiment, the number average molecular weight of the block copolymer is 1000 to 15000, typically 5000 to 15,000, suitably 3000 to 7000.

The incorporation of PEG blocks within the block copolymer alleviate the hydrophobic PPG parts of the block copolymer.

Generally the block copolymer has the general structure PEG-PPG-PEG. Accordingly the PEG blocks are at the terminal ends of the block copolymer and have primary hydroxyls that react much faster than secondary hydroxyls (such as those found in the PPG portion).

Suitable block copolymers are available under the trade name Pluronic®, including Pluronic® P-123.

Polyacrylic Add Salt

The formulation includes 0.1 to 5 wt. % of at least one polyacrylic acid salt, generally a polyacrylic acid alkali metal salt, generally a polyacrylic acid sodium salt, a polyacrylic acid potassium salt or a combination thereof, typically a polyacrylic acid sodium salt.

The polyacrylic acid salt may have a number average molecular weight of less than 50,000, suitably less than 40,000. According to one embodiment, the number average molecular weight of the polyacrylic acid salt is 1000 to 30000, generally 5000 to 30000, suitably 10,000 to 20,000, typically around 15000.

The formulation generally comprises 0.3 to 2 wt. %, generally 0.2 to 1 wt. %, suitably 0.2 to 0.7 wt. % of polyacrylic acid salt. Polyacrylic acid (PAA) will form ionized surfaces which are expected to provide a lower contact angle. Urethane/PEG compositions have been found in the past to form complexes with PAA. It is expected that this polymer would become permanently bound to PEG compositions and should provide strong ionic charge stabilization. It is expected that the adsorbed and bound polymer would be ionized at pH values from 6.0-8.0 leading to a low contact angle.

Propoxylated Ethylenediamine Compound

The formulation comprises 0.01 to 3 wt. % of at least one propoxylated ethylenediamine compound.

The propoxylated ethylenediamine compound generally has the structure of Formula A:

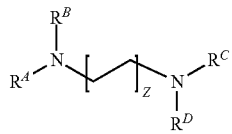

where at least one, typically at least two, suitably at least three, generally all of $R^A$ to $R^D$ have the structure of R below;
where any of $R^A$ to $R^D$ do not have the structure of R below, they represent a hydrocarbyl compound (generally a diamine hydrocarbyl compound) or H;
Z is an integer of from 1 to 10, generally 1 to 5, suitably 1 or 2, typically 1;
the hydrocarbon backbone of the structure of the propoxylated ethylenediamine compound of Formula A may be substituted or unsubstituted (for instance substituted with one or more small alkyl groups).
Where R is:

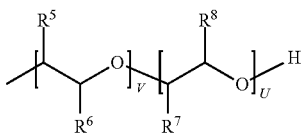

where $R^5$ to $R^8$ independently represent a small alkyl group or H, where at least one of $R^5$ to $R^8$ represents a small alkyl group, typically $C_1$ to $C_5$ alkyl group, generally methyl;
V and U are integers independently selected from 1 to 100, generally independently selected from 30 to 100, typically independently selected from 20 to 60, suitably independently selected from 50 to 100.

Generally the sum of V and U is 150 or less, generally 120 or less, suitably 75 or less.

According to one embodiment, the propoxylated ethylene diamine compound has the structure of Formula Ai or Formula Aii:

Formula Ai:

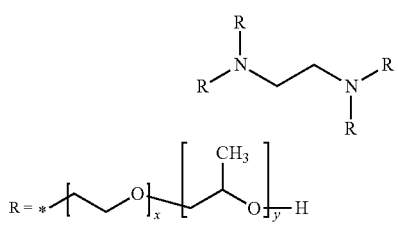

Formula Aii:

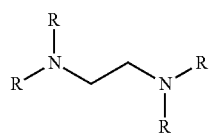

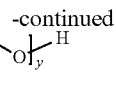

In such embodiments, each R groups may be the same or different, that is Y and U of each R group are independently selected.

Suitably the ratio of polyethylene glycol (PEG) blocks to polypropylene glycol (PPG) blocks is 40-60:60-40, suitably 55-60:45-40.

The propoxylated ethylenediamine compound comprises a poly(ethylene glycol) (PEG) portion and a poly(propylene glycol) (PPG).

Generally one of the $R^5$ to $R^8$ groups represents a small alkyl groups, typically methyl or ethyl, suitably methyl. Preferably all of the other $R^5$ to $R^8$ groups represent H.

According to one embodiment, $R^7$ or $R^8$ represent methyl and all of the other $R^5$ to $R^8$ groups represent H, resulting in a PEG-PPG-diamine structure.

According to a further embodiment, $R^5$ or $R^6$ represent methyl and all of the other $R^5$ to $R^8$ groups represent H, resulting in a PPG-PEG-diamine structure.

According to one embodiment the number average molecular weight of the propoxylated ethylenediamine compound is less than 30,000, generally less than 25,000, suitably less than 20,000, typically less than 15,000. According to one embodiment the number average molecular weight of the propoxylated ethylenediamine compound is more than 1000, generally more than 3000, suitably more than 5000.

According to one embodiment, the number average molecular weight of the propoxylated ethylenediamine compound is 5000 to 10,000, typically 6000 to 8000. According to one embodiment, the number average molecular weight of the number average molecular weight of the propoxylated ethylenediamine compound is 12000 to 17000, typically 14000 to 16000.

Suitable propoxylated ethylenediamine compound include ethylenediaminetetrakis(ethoxylate-block-propoxylate) tetrol. Mention may be made of compounds available under the trade name Tetronic, including Tetronic 90R4.

Generally, the formulation includes 0.05 to 1 wt. %, generally around 0.1 wt. % of at least one propoxylated ethylenediamine compound.

Whilst the applicant does not wish to be bound by theory, it is believed that the inclusion of the propoxylated ethylenediamine compound improves the stability of the formulation of the present invention. The rate of degradation of the formulation of the present invention is slower than comparative formulations without propoxylated ethylenediamine compound. This may be due to reaction of the amine in the propoxylated ethylenediamine compound with any peroxide radicals formed, improving the shelf life stability of the formulation of the present invention.

According to one embodiment, the formulation comprises 5 wt. % or less of the sum of at least one block copolymer of ethylene oxide-propylene oxide-ethylene oxide, at least one polyacrylic acid salt and at least one propoxylated ethylenediamine compound, generally 4 wt. % or less, suitably 3 wt. % or less, typically 2 wt. % or less.

Phosphate Containing Compound

According to one embodiment, the formulation of the present invention may comprise a compound including one or more phosphate groups. Typically, the compound including one or more phosphate groups may include one to three phosphate groups.

According to one embodiment, the compound including one or more phosphate groups may comprise a hydrophilic head group (for example a choline head group) and one or more hydrophobic phosphate containing tail group(s). According to one embodiment, the compound including one or more phosphate groups comprises a choline group (for instance glycerol phosphorylcholine (GPC)).

The compound including one or more phosphate groups may be a phospholipid. Phospholipids are phosphorus-containing lipids composed primarily of fatty acid chains, a phosphate group and a nitrogenous base.

The phospholipids may be those disclosed in WO2008/144494 which is incorporated herein by reference.

The phospholipids of the present invention generally include a phosphate group linked to a quaternary ammonium functionality via an optionally substituted hydrocarbyl group, generally an aliphatic hydrocarbon group (e.g. $C_{1-6}$ alkyl, alkenyl, alkynyl), in particular an optionally substituted alkenyl group, typically $C_{1-6}$ alkenyl, suitably an optionally substituted propylene group. The quaternary ammonium functionality is further linked to at least one optionally substituted hydrocarbyl group, generally an aliphatic hydrocarbon group (e.g. alkyl, alkenyl, alkynyl), in particular an optionally substituted $C_{1-30}$ alkyl group.

The phospholipids of the present invention tend to be highly water soluble.

According to one embodiment, the phospholipids are of the formula:

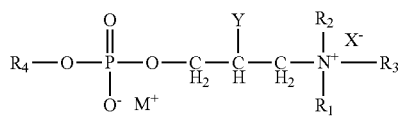

wherein:
each of $R_1$ and $R_3$ independently represents an alkyl group (generally $C_{1\ to\ 6}$ alkyl):
$R_2$ is selected from the group consisting of hydrogen and $C_{1\ to\ 30}$ alkyl (generally $C_{1\ to\ 6}$ alkyl), optionally substituted by $NHC(=O)-(CH_2)_{10}CH_3$ or $NHC(=O))-(CH_2)_{12}CH_3$;

$R_4$ is selected from the group consisting of hydrogen and $CH_2CH(Y)CH_2N^+ R_1R_2R_3X^-$ wherein
$R_1$, $R_2$ and $R_3$ are as defined above;
X is halo;
Y is selected from the group consisting of OH, O—($C_{1\ to\ 10}$)-alkyl and O—($C_{1\ to\ 10}$)-alkenyl; and
M is selected from the group consisting of sodium and potassium.

Generally, $R_1$ and $R_3$ both represent methyl

Typically, $R_2$ represents $C_{12}$ alkyl group, $C_{1\ to\ 6}$ alkyl substituted by $NHC(=O)-(CH_2)_{10}CH_3$ or $NHC(=O)-(CH_2)_{12}CH_3C$. According to one embodiment, $R_2$ represents an unsubstituted $C_{12}$ alkyl group, $(CH_2)_3NHC(=O)-(CH_2)_{10}CH_3$, or $(CH_2)_3NHC(-CH_2)_{12}CH_3C$.

Suitably $R_4$ represents $CH_2CH(Y)CH_2N^+ R_1R_2R_3X^-$.

According to one embodiment, $R_1$ and $R_3$ both represent methyl, $R_2$ represents $C_{12}$ alkyl group, and $R_4$ represents $CH_2CH(OH)CH_2N^+(CH_3)_2(CH_2)_{11}CH_3$, X– represents Cl⁻, Y represents OH⁻ and M⁺ represents Na⁺.

According to one embodiment, $R_1$ and $R_3$ both represent methyl, $R_2$ represents $(CH_2)_3NHC(=O)-(CH_2)_{10}CH_3$, $R_4$ represents $CH_2CH(OH)CH_2N^+(CH_3)_2(CH_2)_3NHC(O)(CH_2)_{10}CH_3$, X– represents Cl⁻, Y represents OH⁻ and M⁺ represents Na⁺.

According to one embodiment, $R_1$ and $R_3$ both represent methyl, $R_2$ represents $(CH_2)_3NHC(=O)-(CH_2)_{10}CH_3$, $R_4$ represents $CH_2CH(OH)CH_2N^+(CH_3)_2(CH_2)_3NHC(O)(CH_2)_{12}CH_3$, X– represents Cl⁻, Y represents OH⁻ and M⁺ represents Na⁺.

According to one embodiment, the formulation includes the phospholipid Cocamidopropyl PG-Dimonium Chloride Phosphate (also referred to as Tris(N—C5-17-alkylamidopropyl-N,N-dimethyl-N-(2-hydroxypropyl)ammonio) phosphate trichloride), with the structure:

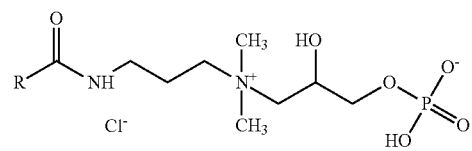

R: coco-alkyl.

According to a further embodiment, the formulation includes the phospholipid Myristamidopropyl PG-Dimonium Chloride Phosphate, with the structure:

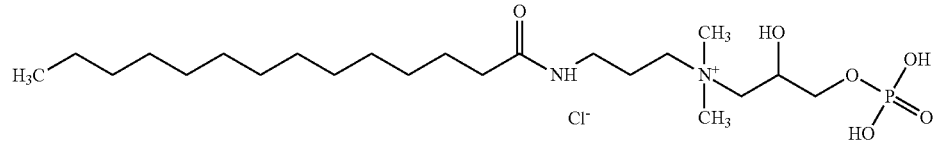 [SMILES: CCCCCCCCCCCCCC(=O)NCCC[N+](C)(C)CC(O)COP(=O)(O)O ; [Cl-]]

According to a further embodiment, the formulation includes the phospholipid Linoleamidopropyl PG-Dimonium Chloride Phosphate with the structure:

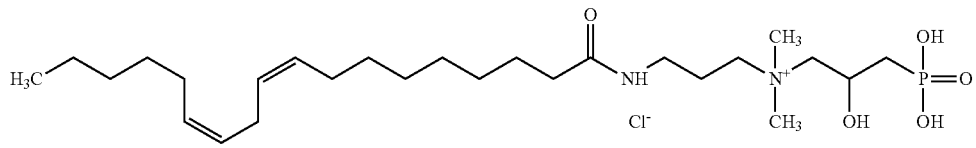 [SMILES: CCCCC/C=C\C/C=C\CCCCCCCC(=O)NCCC[N+](C)(C)CC(O)CP(=O)(O)O ; [Cl-]]

Arlasilk Phospholipid EFA-LQ-(AP) also includes Propylene Glycol and Water.

According to one embodiment, the formulation comprises 0.001% to 2% phospholipid, generally 0.5 to 1.5%, suitably around 1% phospholipid.

Phosphate Containing Compound Pre-Treatment

According to one embodiment, the article to be treated is contacted with a formulation including one or more phosphate groups prior to contact with the formulation of the present invention.

The compound containing one or more phosphate groups is as described above.

Generally, the compound containing one or more phosphate groups is a phospholipid.

The phospholipids are as described above.

Typically, the phospholipid pre-treatment formulation comprises 0.001% to 2% phospholipid, generally 0.5 to 1.5%, suitably around 1% phospholipid.

According to one embodiment, the phospholipid pre-treatment formulation includes one or more polyethylene compounds. Generally, the polyethylene compounds are as described herein, typically at the amounts described herein.

The article may be contacted with a solvent prior to contact with the phospholipid pre-treatment formulation and/or prior to contact with the formulation of the present invention. Suitable solvents include alcohols, such as isopropyl alcohol, and heptane.

Polyethylene Glycol

According to one embodiment, the formulations include one or more polyethylene glycol compound.

Generally, the formulation may include more than one polyethylene glycol compound. Suitably the formulation includes at least one low molecular weight polyethylene glycol compound, having a number average molecular weight of less than 1000.

According to one embodiment, the formulation may include more than one low molecular weight polyethylene glycol compound The formulation may include a low molecular weight polyethylene glycol compound, having a number average molecular weight of less than 1000, and a high molecular weight polyethylene glycol compound, having a number average molecular weight of more than 4000.

According to one embodiment, the formulation may include more than one low molecular weight polyethylene glycol compound and a high molecular weight polyethylene glycol compound.

Suitably the low molecular weight polyethylene glycol has a number average molecular weight of 900 or less, typically, 100 to 800, generally, 150 to 500. The low molecular weight polyethylene glycol compound may have a number average molecular weight of 200+/−10%, or 300+/−10%.

The high molecular weight polyethylene glycol compound may have a number average molecular weight of 4500 to 10,000, typically 5000 to 7000, suitably 5500 to 6500.

The high molecular weight polyethylene glycol compound may have a number average molecular weight of 6000+/−10%.

According to one embodiment, the formulation includes a low molecular weight polyethylene glycol compound, having a number average molecular weight of around 200 or around 300 and a high molecular weight polyethylene glycol compound, having a number average molecular weight of around 6000.

The formulation may include a first low molecular weight polyethylene glycol compound, having a number average molecular weight of around 200, a second low molecular weight polyethylene glycol compound, having a number average molecular weight of around 300 and a high molecular weight polyethylene glycol compound, having a number average molecular weight of around 6000.

The formulation generally includes 1 to 5 g polyethylene glycol per 100 ml formulation. Typically, each polyethylene glycol compound is present at an amount of 0.5 to 2 g per 100 ml formulation.

Polyethylene Glycol Pre-Treatment

According to one embodiment, the article to be treated is contacted with a formulation including one or more polyethylene glycol compounds prior to contact with the formulation of the present invention.

The polyethylene glycol(s) may be present in the phospholipid pre-treatment formulation or may be in the form of a separate polyethylene glycol pre-treatment.

The polyethylene glycol(s) are generally as described above and are suitably provided in the pre-treatment formulation in the amounts detailed above.

Alternatively, or additionally, the article to be treated may be contacted with a solvent prior to contact with the formulation including one or more polyethylene glycol compounds and/or the formulation of the present invention. Suitable solvents include alcohols, such as isopropyl alcohol and heptane.

Additional Components

According to one embodiment, the formulation comprises 0.5 to 2 wt. % alkali metal salt, generally a sodium or potassium salt, generally sodium chloride or potassium chloride or a combination thereof. Generally, the formulation includes 0.7 to 1.5 wt. % alkali metal salt.

The formulation may include one or more buffers. The skilled man will be well aware of suitable buffers.

Mention may be made of weak acids and conjugate base, generally an acid having an associated pKa of 9.5 to 10. Mention may be made of boric acid and borate, in particular an alkali metal borate salt such as sodium borate. Mention may be made of sodium di-Tertborate.

According to one embodiment, the formulation comprises 0.01 to 0.5 wt. % boric acid, typically 0.05 to 0.2 wt. %, and 0.001 to 0.02 wt. % alkali metal borate salt.

The buffer may comprise an alkali metal phosphate, an alkali metal carbonate, or a mixture thereof. The alkali metal may comprise sodium or potassium. The buffer may comprise one or more of monosodium phosphate, disodium phosphate, trisodium phosphate, monopotassium phosphate, dipotassium phosphate, tripotassium phosphate, sodium carbonate, sodium bicarbonate, or a mixture of two or more thereof. Disodium phosphate may be used.

One or more pH modifiers may be included in the formulation.

The formulation may optionally comprise one or more surfactants, in particular non-ionic surfactants. The surfactant(s) may be associated with anti-microbial or disinfectant properties.

The surfactant may comprise a wetting agent, emulsifier, foaming agent and/or dispersant. The surfactant may comprise a compound that contains at least one hydrophobic group and at least one hydrophilic group. The surfactant may comprise both a water insoluble (or oil soluble) component and a water soluble component. The surfactant may comprise one or more ionic (e.g., anionic, cationic and/or zwitterionie) and/or nonionic compounds. The surfactant may comprise one or more polyethylene glycol ethers, alkylarylsulfonates, amine oxides, poly(oxyalkylene) compounds, block copolymers comprising alkylene oxide repeat units, carboxylated alcohol ethoxylates, ethoxylated alkyl phenols, ethoxylated amines, ethoxylated amides, oxiranes, ethoxylated fatty acids, ethoxylated fatty esters, ethoxylated oils, fatty esters, fatty acid amides, glycerol esters, glycol esters, sorbitan esters, imidazoline and/or derivatives thereof, lecithin and/or derivatives thereof, lignin and/or derivatives thereof, glycerides and/or derivatives thereof, olefin sulfonates, phosphate esters and/or derivatives thereof, propoxylated and/or ethoxylated fatty acids and/or alcohols, alkyl phenols, sorbitan and/or derivatives thereof, sucrose esters and/or derivatives thereof, sulfates and/or alcohols and/or ethoxylated alcohols of fatty esters, sulfonates of dodecyl and/or tridecyl benzenes, condensed naphthalenes, sulfosuccinates and/or derivatives thereof, tridecyl and/or dodecyl benzene sulfonic acids, mixtures of two or more thereof, and the like.

Suitable surfactants are available under the trade name Poloxamer®.

One or more emulsifier, thickener, binder or suspending agent may be included in the formulation.

In one embodiment, a cellulose derivative is included such as HPMC.

The formulation may include an additional component having disinfectant properties.

According to one embodiment, the formulation may include polyvinylpyrrolidone.

In one embodiment, the formulation further comprises one or more antioxidants. Suitable antioxidants include those generally used for polyurethanes which may be reactive or non-reactive with other components of the composition. These include BHA (butylated hydroxy anisole), BHT (butylated hydroxytoluene) and ascorbic acid etc. Suitably, the antioxidant is BHA.

Generally, the antioxidant is used in an amount of about 0.01 to about 1 wt. % of the formulation, typically from about 0.2 to about 0.5 wt. % of the formulation. More than one antioxidant and/or synergistic antioxidant may also be used in the formulation as suited for the product.

In one embodiment, formulation of the invention comprises one or more additional components such as plasticiser, humectant, lubricant, process aid, viscosity reducer or diluent including compatibility enhancer diluents. Generally the formulation of the present invention comprises less than 5 wt. % of the sum of these additional components.

Methods and Uses

According to one aspect of the present invention, the formulation may be suitable for use as a treatment formulation, in particular for a medical device. The treatment formulation generally reduces or prevents contamination of the device by micro-organisms.

There is also provided a method of treating an article (such as a medical device) by contacting at least one surface of the article with the formulation as described herein.

Such methods and uses generally reduce the associated contact angle of the surface of the article, increase wettability and increase the biocompatibility of the article for use on or in the human body. Comfort of wear is increased accordingly, both initial comfort of wear and comfort following extended periods of contact between the article and a surface of the human body.

The methods and uses provided herein generally result in the reduction or prevention of binding of proteins and/or lipids to the treated surface. Additionally, or alternatively, the methods and uses may result in the reduction of platelet aggregation on or at the treated surface.

The methods and uses provided herein generally result in the reduction or prevention of contamination of the treated surfaces with micro-organisms.

The methods and uses provided herein generally result in the reduction or prevention of the formation of biofilms on the treated surfaces.

There is provided an article, in particular a medical device, comprising the formulation described herein, in particular a receptacle including the medical device surrounded by the formulation of the present invention.

According to one embodiment, there is provided a method of reducing or preventing contamination of articles by microorganisms comprising contacting the article with the formulation as described herein.

The method may include contacting the article with a pre-treatment formulation including one or more phospholipids prior to contacting the article with the formulation as described herein. The pre-treatment formulation including one or more phospholipids is generally as described above.

The method may also optionally or alternatively include contacting the article with a pre-treatment formulation including one or more solvents and/or a pre-treatment formulation comprising one or more polyethylene glycol compounds prior to contacting the article with the formulation as described herein. The pre-treatment formulation including one or more solvents and the pre-treatment formulation comprising one or more polyethylene glycol compounds is generally as described above.

Typically, the method includes contacting the article with a pre-treatment formulation including one or more solvents, contacting the article with a pre-treatment formulation including one or more polyethylene glycol compounds, and subsequently contacting the article with the formulation as described herein.

Alternatively, the method includes contacting the article with a pre-treatment formulation including one or more solvents, contacting the article with a pre-treatment formulation including one or more phospholipids, and subsequently contacting the article with the formulation as described herein.

According to one embodiment, the method includes includes contacting the article with a pre-treatment formulation including one or more solvents, contacting the article with a pre-treatment formulation including one or more phospholipids, contacting the article with a pre-treatment formulation including one or more polyethylene glycol compounds and subsequently contacting the article with the formulation as described herein.

According to one aspect of the present invention, there is provided a method of reducing the contact angle of a surface by applying the formulation described herein to the surface.

As detailed above, contacting one or more surfaces of an article with the formulation of the present invention reduces the contact angle of the treated surface(s), and thus improves the associated wettability.

The formulation may be for use in reducing the adhesion of micro-organisms to the treated surface(s) and/or reducing the risk of formation of a biofilm on the treated surface(s) of the article.

According to one aspect of the present invention, there is provided a method of reducing platelet aggregation on or at a surface by applying the formulation described herein to the surface.

The formulation may be for use in reducing platelet aggregation on or at the treated surface(s) of the article and reducing the propensity of formation of thrombosis or blood clots on or at the treated surface(s) of the article.

The formulation may be for use in reducing the biostatic associated with the treated surface(s) of the article.

Whilst the applicant does not wish to be bound by theory, it is believed that the formulations described herein reduce protein and/or lipid binding to surface(s) of the article which have been treated with the formulation. In addition, the formulation of the present invention is associated with biocidal and anti-biostatic properties.

As noted above, the method may include contacting the article with one or more pre-treatments prior to contact with the formulations of the present invention, in particular, one or more of the phospholipid pre-treatment formulation and the polyethylene glycol pre-treatment formulation.

According to one embodiment, the method may include the step of contacting the article with solvents such as heptane or isopropyl alcohol prior to contact with the formulations of the present invention.

Suitable articles are generally formed from a polymeric material, such as a polyurethane, in particular a PEG based polyurethane. The polymeric material may comprise silicone.

Medical devices of particular interest include any which are intended for contact with a biological fluid, in particular, biological fluid selected from the group consisting of blood, urine, tears, saliva and mucous.

The article to be treated may be medical, dental, pharmaceutical, veterinary or mortuary instruments and devices.

According to one aspect, the medical device may be an ophthalmic device, such as a contact lens (hard or soft), an intraocular lens, a corneal onlay, other ophthalmic devices (e.g., strips, or the like) used on or about the eye or ocular vicinity.

According to one embodiment, the medical device may be selected from the group consisting of stents, catheters, peritoneal dialysis tubing, draining devices, joint prostheses, implants such as cardiac implants, including heart valves, thrombus filters, endoscopes and dental devices, dental implants, for example fillers, vascular catheter for instance for use in chronic haemodialysis, acute haemodialysis, haemofiltration, or extracorporeal $CO_2$ removal, extra corporeal circuitry, scalpel and shunts.

In a further aspect of the invention there is provided a substrate to which the formulation of the invention is applied or attached. The substrate is suitable for application to wounds or delivery to wound sites. Preferably, the substrate allows for the transfer of the active agents of the product of the invention from the substrate to a wound bed to achieve their antibiofilm effect. The substrate may be a dressing, for example, wound dressing. The dressing may comprise a fabric material or it may be a collagen-like material.

The invention provides a method of preventing biofilm formation in an environment comprising the step of administering to the formulation according to the invention. The method may be in vivo or ex vivo.

There is provided the use of the formulation described herein in the treatment or prevention of a microbial infection or disease, in particular a microbial biofilm.

There is also provided a method of preventing biofilm formation on or in an article, in particular a medical device comprising administering the formulation as described herein to at least one surface of the medical device, or providing the formulation as described herein on at least one surface of the medical device.

Generally at least 1 mL of the formulation is provided per $cm^2$ of the surface.

The method of the invention may be used to prevent or restrict the formation of a biofilm in the human body especially in the treatment of microbial infections. Conditions associated with biofilm infections may include topical infections, oral infections and systemic infections.

Topical infections may include wounds, ulcers and lesions for example, cutaneous wounds such as cuts or burns, and conditions associated therewith.

The biofilm may comprise any biofilm forming microorganism selected from bacteria, fungi, yeast, viruses and protozoa. Typically the microorganism is a bacterium for example a Gram-positive or Gram-negative bacterium. The bacterium may include *Pseudomonas* spp., for example *Pseudomonas aeruginosa*; *Staphylococcus* spp., for example *Staphylococcus aureus* and *Staphylococcus epidermidis*; *Haemophilus* spp., for example *Haemophilus influenza*; *Burkholderia* spp., for example *Burkholderia cepacia*; *Streptococcus* spp., *Propionibacterium* spp., for example *Propionibacterium acnes*. Preferably the bacterium is selected from *Pseudomonas* spp., for example *Pseudomonas aeruginosa* and *Staphylococcus* spp., for example *Staphylococcus aureus* and *Staphylococcus epidermidis*.

The method of the invention may be used to minimise and, preferably, prevent the formation of biofilms in a variety of environments including, but not limited to, household, workplace, laboratory, industrial environment, aquatic environment (e.g. pipeline systems), medical devices including indwelling devices, Specific Formulations According to one embodiment there is provided a formulation comprising, consisting or consisting essentially of:
  a, 0.1 to 7 wt. % of at least one block copolymer of ethylene oxide and propylene oxide, generally having the structure of ethylene oxide-propylene oxide-ethylene oxide;
  b. 0.1 to 5 wt. % of at least one polyacrylic acid salt;
  c. 0.01 to 3 wt. % of at least one propoxylated ethylenediamine compound, generally having the structure of Formula A, Formula Ai or Formula Aii;
  d. 0.5 to 2 wt. % alkali metal salt,
  e. at least 90 wt. % water,
  f. optionally up to 5 wt. % additional components such as buffers and surfactants.

According to one embodiment, the formulation comprises, consists or consists essentially of:
  a. 0.1 to 7 wt. % of at least one block copolymer of ethylene oxide and propylene oxide, generally having the structure of ethylene oxide-propylene oxide-ethylene oxide;
  b. 0.1 to 5 wt. % of at least one polyacrylic acid salt;
  c. 0.01 to 3 wt. % of at least one propoxylated ethylenediamine compound, generally having the structure of Formula A, Formula Ai or Formula Aii;
  d. 0.5 to 2 wt. % alkali metal salt,
  e. at least 90 wt. % water,
  f. optionally up to 5 wt. % additional components such as buffers and surfactants
  g. up to 1.5% of a phospholipid, preferably selected from the group consisting of Cocamidopropyl PG-Dimonium Chloride Phosphate, Myristamidopropyl PG-Dimonium Chloride Phosphate, and Linoleamidopropyl PG-Dimonium Chloride Phosphate.

An exemplary formulation of the present invention comprises, consists of or consists essentially of:
  a. 0.2 to 5 wt. % of at least one block copolymer of ethylene oxide and propylene oxide comprising 50 to 80% propylene oxide;

b. 0.3 to 1 wt. % polyacrylic acid alkali metal salt, generally a polyacrylic acid sodium salt;
c. 0.05 to 1 wt. % of at least one propoxylated ethylenediamine compound having the structure of Formula A, Formula Ai or Formula Aii having a number average molecular weight of less than 30,000;
d. 0.5 to 2 wt. % sodium chloride, potassium chloride or a mixture thereof;
e. at least 90 wt. % water,
f. optionally up to 5 wt. % additional components such as buffers and surfactants.

Suitably the formulation includes up to 1.5% phospholipid, in particular selected from the group consisting of Cocamidopropyl PG-Dimonium Chloride Phosphate, Myristamidopropyl PG-Dimonium Chloride Phosphate, and Linoleamidopropyl PG-Dimonium Chloride Phosphate.

Generally, the components listed above form 100 wt. % of the formulation.

Alternatively, the components listed above may form up to 95 wt. % of the formulation, with the remaining reactant mixture being formed from additional components as described herein.

Kit

According to a further embodiment there is provided a kit of parts including a receptacle containing the formulation as described herein and instructions for use.

The kit may include one or more pre-treatment formulations, in particular one or more of a phospholipid pre-treatment formulation, a polyethylene glycol formulation and/or a solvent.

Generally the kit comprises a phospholipid pre-treatment formulation, a polyethylene glycol formulation and a solvent.

The kit may include an instrument for application of the formulation, for instance a spray attachment, spatula, syringe and equivalent.

Kits can further include instructions for performing the methods described herein and/or interpreting the results, in accordance with any regulatory requirements. In addition, software can be included in the kit for analysing the detected micro-organism level, and/or the contact angle of a surface. Preferably, the kits are packaged in a container suitable for commercial distribution, sale, and/or use, containing the appropriate labels, for example, labels including the identification of the chemical reactants included.

The present invention will now be described by way of example only.

Example 1

The following formulation was prepared according to the method provided below where:

To Prepare 9 Litres of Saline
  9 g—0.1 wt. % of propoxylated ethylenediamine compound according to Formula Ai having a number average molecular weight of 7200 (generally the compound sold under the trade name Tetronic® 90R4);
  45 g—0.5 wt. % block copolymer of ethylene oxide and propylene oxide (PEG-PPG-PEG) having a number average molecular weight of 5800 (generally the compound sold under the trade name Pluronic® 123);
  36 g—0.4 wt. % of Polyacrylic Acid (PAA) Sodium Salt having a number average molecular weight of 15000;
  81 g—0.9 wt. % of Sodium Chloride;
  9.9 g—0.1 wt. % of Boric Acid;
  0.99 g—0.01 wt. % of Sodium di-Tertborate
  0.45 g—0.005 wt % non-ionic, hydrophilic surfactant such as that sold under the trade name Poloxamer 407.
  8910 mL of deionised water—98 wt %

1. Measure 946 ml of deionised water into the Duran bottle using a measuring cylinders).
2. Weigh out 9 g of the propoxylated ethylenediamine compound (+/−0.1 g) into the Duran bottle. Record the amount added.
3. Mix the solution with a magnetic stirrer on medium speed until fully dissolved (~15 min).
4. Weigh out 45 g of the block copolymer of ethylene oxide and propylene oxide (+/−0.1 g) into the solution. Record the amount added.
5. Shake well and place in fridge for an overnight, shake between whiles until completely dissolved.
6. Next day, mix the solution with a magnetic stirrer on medium speed (~30 min).
7. Measure 5 litres of deionised water into a clean dry carboy using a measuring cylinder.
8. Add Duran containing water, propoxylated ethylenedi amine compound and block copolymer of ethylene oxide and propylene oxide into the carboy.
9. Add an additional 1 litre of deionised water to wash out Duran containing propoxylated ethylenedi amine compound and block copolymer of ethylene oxide and propylene oxide and add washings to carboy.
10. Measure 964 ml of deionised water into a clean dry Duran bottle using a measuring cylinders).
11. Weigh out 36 g of PAA Sodium Salt (+/−0.1 g) into the Duran bottle. Record the amount added.
12. Mix the solution with a magnetic stirrer on medium speed until fully dissolved (~15 min).
13. Add Duran containing water and PAA Sodium Salt into the carboy.
14. Add an additional 1 litre of deionised water to wash out Duran containing PAA Sodium Salt and add washings to carboy.
15. Weigh 81 g Sodium Chloride (+/−0.1 g) and add to the water. Record the amount added.
16. Weigh 9.9 g Boric Acid (+/−0.1 g) and add to the water. Record the amount added.
17. Weigh 0.99 g Sodium di-Tetraborate (+/−0.01 g) and add to the water. Record the amount added.
18. Weigh 0.45 g the surfactant (+/−0.01 g) and add to the saline. Record the amount added.
19. Mix the solution with a magnetic stirrer on medium speed until fully dissolved (~30 min).
20. Check pH of the solution and record this. Ensure that solution is within specification 6.8-7.8. If not reject the solution.
21. Degas with Nitrogen for 60 minutes in a fume hood. Inspect the saline carboy and ensure a reasonable volume of gas is bubbling through the solution throughout the process.
22. Filter saline through a 0.45 μm Vacucap filter into clean glass duran bottles (≤1 L), then autoclave.

Example 2

The following solutions were prepared:
Saline 6
  To prepare 9 Litres of Saline B
  81 g of Sodium Chloride—0.89 wt %
  9.9 g of Boric Acid—0.11 wt %
  0.99 g of Sodium di-Tertborate—0.011 wt %
  0.45 g Poloxamer 407—0.005 wt %
  9000 mL of deionised water—99 wt %

Saline E
  To prepare 9 Litres of Saline E
  9 g of Tetronic 90R4 (Mn 7200)—0.1 wt %
  45 g Pluronic 123 (Mn 5800)—0.5 wt %
  36 g of Polyacrylic acid Sodium Salt (Mw 15000)—0.4 wt %
  81 g of Sodium Chloride—0.9 wt %
  9.9 g of Boric Acid—0.1 wt %
  0.99 g of Sodium di-Tertborate—0.01 wt %
  0.45 g Poloxamer 407-0.005 wt %
  8910 mL of deionised water—98 wt %
Saline F
  To prepare 9 Litres of Saline F
  9 g of Tetronic 1107 (Mn)—0.099 wt %
  45 g Pluronic 123 (Mn 5800)—0.49 wt %
  0.6750 g Hydroxpropylmethyl cellulose—0.0074 wt. %
  9 g polyvinylpyrrolidone—0.099 wt %
  54 g of Polyacrylic acid Sodium Salt (Mw 15000)—0.59 wt %
  75.95 g of Sodium Chloride—0.83 wt %
  10.82 g of Boric Acid—0.12 wt %
  0.45 g of Sodium di-Tertborate—0.0049 wt %
  0.45 g Poloxamer 407-0.0049 wt %
  8901 mL of deionised water—97.74 wt %
Solution I
  Saline B with PEG200 (1 g/100 mL) and PEG6000 (1 g/100 ml).
Solution II
  Saline B with PEG300 (1 g/100 mL) and PEG6000 (1 g/100 ml).
Solution IV.
  Saline B with PEG200 (1 g/100 mL) and PEG300 (1 g/100 mL) and PEG6000 (1 g/100 ml).

Example 2A

Lenses were swollen in heptane for 1 h than transferred into Solution IV for 3 h and transferred and autoclaved in Saline F. The contact angle of the treated lenses was measured at room temperature. The mean contact angle of the treated lens was 18.2 with an associated standard deviation of 5.3.

| Time (min) | Sample 1 | Sample 2 | Sample 3 | Sample 4 | Sample 5 | Sample 6 | Sample 7 | Sample 8 | Sample 9 | Sample 10 |
|---|---|---|---|---|---|---|---|---|---|---|
| Untreated lens | 82.3 | 79.9 | 54.3 | 82.5 | 79.1 | 90.9 | 81.1 | 84.3 | 81.2 | 65.4 |
| 15 to 30 | 13.4 | 13.3 | 68.7 | 28.7 | 14.6 | 20.4 | 16.2 | 15.1 | 22.5 | 14.5 |

Example 2B

Lenses were swollen in heptane for 1 h than transferred into Solution IV for 3 h and transferred and autoclaved in Saline F. The contact angle of the treated lenses was measured at 35° C. The mean contact angle of the treated lens was 22.7 with an associated standard deviation of 4.2.

| Time (min) | Sample 1 | Sample 2 | Sample 3 | Sample 4 | Sample 5 | Sample 6 | Sample 7 | Sample 8 | Sample 9 | Sample 10 |
|---|---|---|---|---|---|---|---|---|---|---|
| Untreated lens | 81.0 | 37.4 | 78.1 | 85.7 | 89 | 56 | 29.3 | 80.3 | 73.7 | 78.7 |
| 15 to 30 | 24.5 | 21.8 | 17.2 | 21.4 | 31.9 | 22.2 | 31.9 | 15.4 | 21.5 | 20.8 |

Example 2C

Lenses were swollen in isopropyl alcohol for 1 h than transferred into Solution I for 3 h and transferred and autoclaved in Saline F. The contact angle of the treated lenses was measured at room temperature. The mean contact angle of the treated lens was 21.6 with an associated standard deviation of 5.8.

| Time (min) | Sample 1 | Sample 2 | Sample 3 | Sample 4 | Sample 5 |
|---|---|---|---|---|---|
| Untreated lens | 97.2 | 75.9 | 88.9 | 75.7 | 79.6 |
| 15 to 30 | 23.3 | 10.7 | 26.36 | 15.1 | 56.1 |

Example 2D

Lenses were swollen in isopropyl alcohol for 1 h than transferred into Solution II for 3 h and transferred and autoclaved in Saline F. The contact angle of the treated lenses was measured at room temperature. The mean contact angle of the treated lens was 21.4 with an associated standard deviation of 0.9,

| Time (min) | Sample 1 | Sample 2 | Sample 3 | Sample 4 | Sample 5 |
|---|---|---|---|---|---|
| Untreated lens | 53.5 | 84.9 | 88.3 | 69.3 | 39.3 |
| 15 to 30 | 22.4 | 36.9 | 16.1 | 20.6 | 21.3 |

Example 2E

Lenses were swollen in isopropyl alcohol for 1 h than transferred into Solution IV for 3 h and transferred and autoclaved in Saline F. The contact angle of the treated lenses was measured at room temperature. The mean contact angle of the treated lens was 18.9 with an associated standard deviation of 1.2.

| Time (min) | Sample 1 | Sample 2 | Sample 3 | Sample 4 | Sample 5 |
|---|---|---|---|---|---|
| Untreated lens | 93.8 | 87.9 | 77.8 | 86.1 | 75.6 |
| 15 to 30 | 20.3 | 18.5 | 17.9 | 31.4 | 14.8 |

Example 3A

Lenses were swollen in a pre-treatment formulation including 1% Phospholipid Linoleamidopropyl PG-Dimonium Chloride Phosphate (structure provided above) including propylene glycol and water in Saline B. The lenses were transferred into Saline F and autoclaved. The contact angle of the treated lenses was measured at room temperature. The mean contact angle of the treated lens was 22.4 with an associated standard deviation of 0.9.

| Time (min) | Sample 1 | Sample 2 | Sample 3 | Sample 4 | Sample 5 |
|---|---|---|---|---|---|
| Untreated lens | 58.0 | 67.3 | 74.9 | 77.2 | 81.9 |
| 15 to 30 | 23.0 | 17.2 | 21.4 | 22.7 | 30.7 |

Example 3B

Lenses were swollen in in a pre-treatment formulation including 1% Phospholipid Cocamidopropyl PG-Dimonium Chloride Phosphate (structure above) in Saline B. The lenses were then transferred into Saline F and autoclaved. The contact angle of the treated Senses was measured at room temperature. The mean contact angle of the treated lens was 22.4 with an associated standard deviation of 1.0.

| Time (min) | Sample 1 | Sample 2 | Sample 3 | Sample 4 | Sample 5 |
|---|---|---|---|---|---|
| Untreated lens | 77.4 | 60.9 | 45.3 | 47.1 | 56 |
| 15 to 30 | 23.7 | 16.5 | 22.4 | 21.4 | 23.4 |

Example 3C

Lenses were swollen in in a pre-treatment formulation including 1% Phospholipid Myristamidopropyl PG-Dimonium Chloride Phosphate (structure above) in Saline B. The lenses were then transferred into Saline F and autoclaved. The contact angle of the treated lenses was measured at room temperature. The mean contact angle of the treated lens was 24.1 with an associated standard deviation of 2.3.

| Time (min) | Sample 1 | Sample 2 | Sample 3 | Sample 4 | Sample 5 |
|---|---|---|---|---|---|
| Untreated lens | 41.5 | 48.2 | 73.1 | 54.5 | 80.5 |
| 15 to 30 | 31.4 | 20.3 | 26.2 | 24.5 | 21.7 |

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

Throughout the description and claims of this specification, the words "comprise" and "contain" and variations of the words, for example "comprising" and "comprises", mean "including but not limited to", and are not intended to (and do not) exclude other moieties, additives, components, integers or steps. All documents referred to herein are incorporated by reference. The word copolymer and block copolymer is used to describe either.

Various modifications and variations of the described aspects of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the relevant fields are intended to be within the scope of the following claims.

The invention claimed is:

1. A formulation comprising:
   a. 0.1 to 7 wt. % of at least one block copolymer of ethylene oxide and propylene oxide having the structure of ethylene oxide-propylene oxide-ethylene oxide;
   b. 0.1 to 5 wt. % of at least one polyacrylic acid salt; and
   c. 0.01 to 3 wt. % of at least one propoxylated ethylenediamine compound.

2. The formulation of claim 1 wherein the at least one propoxylated ethylenediamine compound has the structure of Formula A:

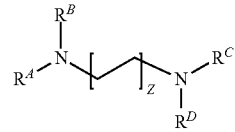

where at least one of $R^A$ to $R^D$ have the structure of R;
where any of $R^A$ to $R^D$ do not have the structure of R below, they represent a hydrocarbyl compound or H;
Z is an integer of from 1 to 10;
the hydrocarbon backbone of the structure of Formula A may be substituted or unsubstituted;
where R is:

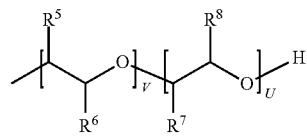

where $R^5$ to $R^8$ independently represent a small alkyl group or H, where at least one of $R^5$ to $R^8$ represents a small alkyl group;
V and U are integers independently selected from 1 to 100.

3. The formulation as claimed in claim 2 wherein the sum of V and U is 150 or less.

4. The formulation of claim 1 wherein each propoxylated ethylenediamine compound has a number average molecular weight of 1000 to 25,000.

5. The formulation of claim 1 wherein the at least one block copolymer of ethylene oxide and propylene oxide comprises 50 to 80 wt. % propylene oxide.

6. The formulation of claim 1 wherein the number average molecular weight of the at least one block copolymer of ethylene oxide and propylene oxide is 1000 to 20,000.

7. The formulation of claim 1 wherein the polyacrylic acid salt is a polyacrylic acid alkali metal salt.

8. The formulation of claim 1 wherein the polyacrylic acid salt has a number average molecular weight of 1000 to 40,000.

9. The formulation of claim 1 comprising a compound including one or more phosphate groups.

10. The formulation of claim 1 including one or more phospholipids of the formula:

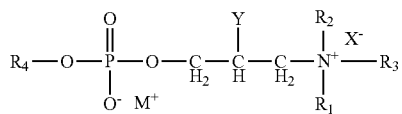

wherein each of $R_1$ and $R_3$ independently represents an alkyl group (generally $C_{1\ to\ 6}$ alkyl);

$R_2$ is selected from the group consisting of hydrogen and $C_{1\ to\ 30}$ alkyl (generally $C_{1\ to\ 6}$ alkyl), optionally substituted by $NHC(=O)-(CH_2)_{10}CH_3$ or $NHC(=O)-(CH_2)_{12}CH_3$;

$R_4$ is selected from the group consisting of hydrogen and $CH_2CH(Y)CH_2N^+R_1R_2R_3X^-$;

X is halo;

Y is selected from the group consisting of OH, $O-(C_{1\ to\ 10})$-alkyl and $O-(C_{1\ to\ 10})$-alkenyl; and M is selected from the group consisting of sodium and potassium.

11. The formulation of claim 10 wherein the phospholipid is selected from the group consisting of Cocamidopropyl PG-Dimonium Chloride Phosphate, Myristamidopropyl PG-Dimonium Chloride Phosphate, and Linoleamidopropyl PG-Dimonium Chloride Phosphate.

* * * * *